United States Patent [19]

Rauscher et al.

[11] Patent Number: 4,943,526
[45] Date of Patent: Jul. 24, 1990

[54] GAMMA-GLUTAMYL-4-AZOANILIDES, PROCESS FOR THE PREPARATION THEREOF AND DIAGNOSTIC AGENTS CONTAINING THEM

[75] Inventors: Elli Rauscher, München, Fed. Rep. of Germany; John Griffiths, Garforth Leeds; Leonard F. Dixon, W. Yorkshire, both of Great Britain

[73] Assignee: Boehringer Mannheim GmbH, Mannheim, Fed. Rep. of Germany

[21] Appl. No.: 231,079

[22] Filed: Aug. 11, 1988

Related U.S. Application Data

[62] Division of Ser. No. 7,077, Jan. 27, 1987, Pat. No. 4,769,447.

[30] Foreign Application Priority Data

Jan. 28, 1986 [DE] Fed. Rep. of Germany ....... 3602443

[51] Int. Cl.$^5$ .......................... C12Q 1/48; C12Q 1/36
[52] U.S. Cl. ........................................ 435/15; 435/24; 435/810
[58] Field of Search ............................ 435/15, 24, 810

[56] References Cited

U.S. PATENT DOCUMENTS 4,560,650 12/1985 Bauer et al. ............................ 435/24

OTHER PUBLICATIONS

Walter, *Methods of Enzymatic Analysis*, vol. V, Bergmeyer (Ed.), Verlay Chemie, Weinheim, 270-277 (1984), 3rd Edition.

*Primary Examiner*—Esther M. Kepplinger
*Attorney, Agent, or Firm*—Felfe & Lynch

[57] ABSTRACT

The present invention provides gamma-glutamyl-4-azoanilides, processes for their preparation and their use as substrates for gamma-glutamyl transferase determination, of the formula

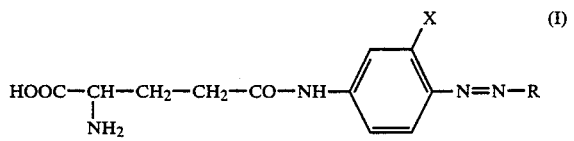

wherein X is alkyl, $-(CH_2)_m-COOH$ or $-O-(CH_2)_n-COOH$ wherein m is 0-4 and n is 1-4; R is optionally substituted p-nitrophenyl; an optionally substituted thiophene residue; an optionally substituted thiazole residue; an optionally substituted benzothiazole residue; an optionally substituted benzoisothiazole residue; an N-alkylthiazole residue; or an optionally substituted 1,3,5-thiodiazole residue; as well as the alkali metal, alkaline earth metal and ammonium salts thereof.

7 Claims, No Drawings

GAMMA-GLUTAMYL-4-AZOANILIDES, PROCESS FOR THE PREPARATION THEREOF AND DIAGNOSTIC AGENTS CONTAINING THEM

This application is a divisional application of U.S. Ser. No. 007,077, filed 01/27/87 now U.S. Pat. No. 4,769,447.

The present invention is concerned with new γ-glutamyl-4-azoanilides, a process for the preparation thereof, diagnostic agents containing them and the use thereof as substrates for the determination of the activity of γ-glutamyl transferase.

The determination of γ-glutamyl transferase (γ-GT) is carried out in clinical-chemical laboratories for the diagnosis of liver diseases. According to a known process, the determination takes place according to the following reaction:

γ-glutamyl-p-nitroanilide +

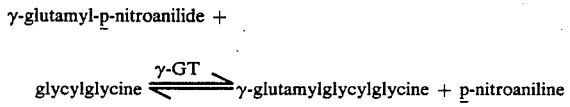

glycylglycine $\xrightleftharpoons{\gamma\text{-GT}}$ γ-glutamylglycylglycine + p-nitroaniline The rate of liberation of the yellow coloured p-nitroaniline can be followed optically. It is a measure of the activity of γ-GT present.

However, the instability and poor solubility of the substrate γ-glutamyl-p-nitroanilide are disadvantageous for the routine use of this process.

These disadvantages can be substantially avoided by the use of γ-glutamyl-4-nitroanilide derivatives substituted in the 3-position by a carboxylic acid or sulphonic acid residue which are described in Federal Republic of Germany Patent Specifications Nos. 22 59 512 and 23 33 798. However, the absorption maxima of these compounds, as well as of the aniline derivatives resulting by the enzymatic fission thereof with γ-GT, lie far below 400 nm. In this wavelength range, the inherent absorption of component materials of the samples, for example bilirubin and materials giving rise to turbidities, already have a noticeable disturbing effect.

Therefore, there is a need for γ-GT substrates which do not display these disadvantages and it is an object of the present invention to satisfy this need.

Thus, according to the present invention, there are provided new γ-glutamyl-4-azoanilides of the general formula:

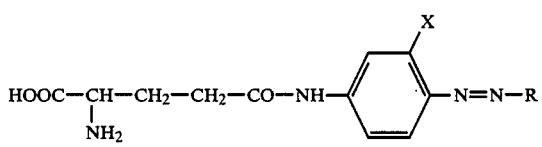

wherein X is an alkyl, —(CH$_2$)$_m$—COOH or —O—(CH$_2$)$_n$—COOH radical, R is a p-nitrophenyl radical which is optionally substituted one or more times by halogen, cyano, alkoxy, hydroxyl, alkyl, carboxyalkyl, amino, alkylamino or dialkylamino, the substituents being the same or different; or R is a thiophene residue which is optionally substituted one or more times by cyano, nitro, alkyl or carboxyalkyl, the substituents being the same or different; or R is a thiazole residue which is optionally substituted one or more times by cyano, carboxyl or alkyl, the substituents being the same or different; or R is a benzothiazole residue which can be substituted one or more times by alkoxy; or R is a benzoisothiazole residue which is optionally substituted one or more times by nitro; or R is an N-alkylthiazole residue or is a 1,3,4-thiodiazole residue which is optionally substituted one or more times by alkylthio, m is 0 or an integer of from 1 to 4 and n is an integer of from 1 to 4; as well as the alkali metal, alkaline earth metal and ammonium salts thereof.

The alkali metal salts can be the lithium, sodium, potassium, rubidium or caesium salts, the lithium, sodium and potassium salts being preferred.

The alkaline earth metal salts can be the magnesium, calcium, strontium or barium salts, the magnesium and calcium salts being preferred.

The ammonium salts can be unsubstituted ammonium salts or can also be those containing ammonium ions substituted one to four times by alkyl or aralkyl radicals, the substituents thereby being the same or different. The alkyl radicals can hereby be those containing up to 7 and preferably up to 4 carbon atoms. The preferred aralkyl radical is the benzyl radical. The ammonium ion is especially preferably the unsubstituted ammonium ion.

Halogen as a substituent of R means fluorine, chlorine, bromine or iodine, chlorine and bromine being especially preferred.

By alkyl and alkoxy radicals in the definitions of the substituents of the radicals R and X are to be understood radicals containing up to 7 and preferably up to 4 carbon atoms, especially preferred radicals being the methyl, ethyl, methoxy and ethoxy radicals.

The meanings given for the alkyl radicals also applies to the alkyl moieties present in carboxyalkyl, alkylthio, alkylamino and dialkylamino radicals; in the case of the dialkylamino radicals, the alkyl moieties can be the same or different. In the same way, the alkyl substituents present in the N-alkylthiazole radicals also have the above-given meaning.

Besides a good water-solubility and stability in aqueous solution, the compounds according to the present invention surprisingly display a great difference of the absorption maxima of the substrate and the coloured material liberated therefrom by the action of γ-GT. Thus, for example, the difference of the absorption maxima of the known substrate γ-glutamyl-3-carboxy-4-nitroanilide (γ$_{max.}$ 317 nm) and of the coloured material obtained therefrom, i.e. 3-carboxy-4-nitroaniline (γ$_{max.}$ 380 nm) is 63 nm. In contradistinction thereto, the compounds according to the present invention of general formula (I) display substantially greater differences between the absorption spectra of the substrate and of the coloured material liberated enzymatically therefrom. As a rule, this difference is from 80 to 110 nm.

Furthermore, the coloured materials liberated by the action of γ-GT on the γ-glutamyl-4-azoanilides according to the present invention absorb in a substantially longer wavelength range than the previously known comparable compounds. Therefore, γ-GT determinations with these new compounds are less subject to disturbances in biological samples.

Especially preferred compounds according to the present invention include the following:

2-amino-5-[[4-(2-cyano-4-nitrophenyl)-azo-3-(2-carboxyethyl)-phenyl]-amino-]-5-oxopentanoic acid diammonium salt; λ$_{max.}$=394 nm; Δλ$_{max.}$=94 nm;

2-amino-5-[[3-(2-carboxyethyl)-4-(2,4-dicyano-3-methyl-5-thienyl)-azophenyl]-amino]-5-oxopentanoic acid diammonium salt; λ$_{max.}$=424 nm; Δλ$_{max.}$=106 nm;

2-amino-5-[[3-(2-carboxyethyl)-4-(5-cyano-4-methyl-2-thiazolyl)-azophenyl]-amino]-5-oxopentanoic acid diammonium salt; $\lambda_{max.} = 420$ nm; $\Delta\lambda_{max.} = 100$ nm;

2-amino-5-[[3-(carboxymethoxy)-4-(6-nitro-2,1-benzoisothiazol-3-yl)-azophenyl]-amino]-5-oxopentanoic acid diammonium salt; $\lambda_{max.} = 453$ nm; $\Delta\lambda_{max.} = 107$ nm.

$\Delta\lambda_{max.}$ hereby means the difference between $\lambda_{max.}$ (coloured material) $-\lambda_{max.}$ (substrate).

The γ-glutamyl derivatives of general formula (I) according to the present invention are new compounds.

The preparation of these new compounds is also the subject of the present invention. It takes place by the reaction of amines of the general formula:

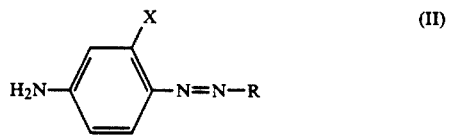

in which X and R have the same meanings as in general formula (I), these amines either being known or being easily prepared by conventional methods, with N-phthaloylglutamic acid anhydride of the formula:

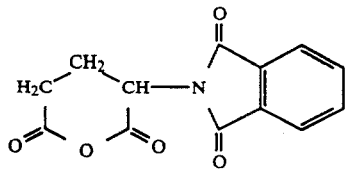

in known manner to give N-phthaloyl-protected γ-glutamyl derivatives of the azo coloured materials of the general formula:

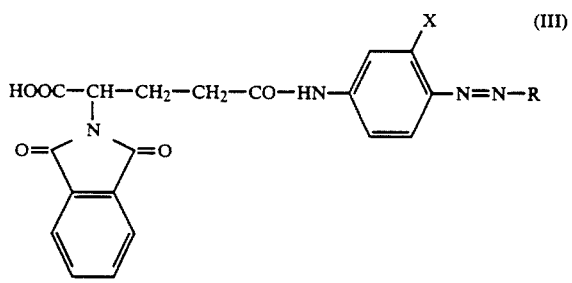

in which X and R have the same meanings as in general formulae (I) and (II), with subsequent removal of the N-phthaloyl protective group. The carboxylic acids hereby obtained can, if desired, be converted by known methods into the salts thereof. Depending upon the reaction conditions used, the salts can also be obtained directly.

The reaction of amines of general formula (II) with N-phthaloylglutamic acid anhydride can take place in lower carboxylic acids, for example formic or acetic acid, acetic acid preferably being used. For the reaction of relatively reactive amines of general formula (II), the aliphatic carboxylic acids used as solvents and activation agents can also be diluted with other polar, aprotic solvents, for example acetone, pyridine, dimethyl sulphoxide or dimethylformamide, acetone being especially preferred. In the case of especially reactive amines of general formula (II), it also suffices to carry out the reaction with N-phthaloylglutamic acid anhydride in polar aprotic solvents which do not react with the amines and anhydrides. In this case, too, acetone has proved to be especially useful. If the amines dissolve only sparingly in acetone as sole solvent, the solubility can be increased especially advantageously by the addition of pyridine.

The amount of ratio of amine to anhydride necessary for the desired reaction depends upon the reactivity of the amines used of general formula (II). It can extend from equimolar to a 100 fold excess of anhydride. Advantageously, there is used a molar ratio of 1:1 to 10:1 of anhydride:amine. The necessary ratio can easily be determined. The reaction temperature can be from about 20° to about 120° C. It depends upon the reactivity of the amine and the solvent used. Thus, for example, reactions in acetone as solvent are advantageously carried out at 20° to 60° C. and especially preferably at 25° to 40° C. Reactions in acetic acid are carried out at temperatures of from 50° to 120° C. and preferably at the reflux temperature of the solvent. Optimum amount ratios of the reaction components, reaction temperature and reaction time can be determined in a simple manner by thin-layer chromatographic monitoring of the reaction on silica gel.

After completion of the reaction, in many cases the product of general formula (III) crystallises out. If no crystallisation takes place, the product can be purified chromatography on silica gel.

For the preparation of the γ-glutamyl derivatives of general formula (I) according to the present invention, the N-phthaloyl protective group must be removed from the compounds of general formula (III). This reaction can be carried out on isolated and purified compounds of general formula (III) but also with the crude product which is obtained from the reaction mixture for the preparation of these compounds by removal of the solvent.

The removal of the N-phthaloyl protective group can take place according to various methods, the use of hydrazine having proved to be especially advantageous. For this purpose, the N-phthaloylglutamyl azo coloured material of general formula (III) is suspended or dissolved in such an amount of a lower alcohol, preferably methanol, that, after completion of the reaction, the totality of the azo compound is present in solution. Subsequently, hydrazine hydrate is added thereto at ambient temperature. When a thin-layer chromatographic control on silica gel shows that the reaction is finished, the mixture is mixed with a ketone in order to bind excess hydrazine. For this purpose, it is preferred to use acetone. To the clear solution obtained is then added an amount of aqueous ammonia solution which is sufficient to precipitate out the N-glutamyl derivative of general formula (I) as ammonium salt. If the precipitation is incomplete, then acetone can be added until the precipitation is complete.

The purification of the compounds thus obtained can take place either by recrystallisation from appropriate solvents, for example water/acetone, or by chromatography on silica gel.

The present invention is also concerned with the use of the compounds of general formula (I) according to the present invention as substrates for the determination of the activity of the enzyme γ-glutamyl transferase (γ-GT).

Furthermore, the present invention also provides diagnostic agents for the determination of the activity of γ-GT which contain at least one compound of general formula (I) according to the present invention.

The determination of the activity of γ-GT with the compounds of general formula (I) according to the present invention can, for example, be carried out according to the following reaction:

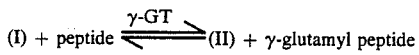

$$(I) + peptide \xrightleftharpoons{\gamma\text{-GT}} (II) + \gamma\text{-glutamyl peptide}$$

γ-GT and compounds of general formula (I) react in aqueous solution with the liberation of an azo coloured material of general formula (II) and transfer of the γ-glutamyl radical to an amino acid or to a peptide. The extinction increase produced by the formation of the coloured material (II) can be determined at an appropriate wavelength. The speed thereof is a measure of the activity of the enzyme.

Because of the greater differences of the absorption maxima of substrate and of enzymatically liberated coloured material and, furthermore, the absorption of the resultant azo coloured material at substantially higher wavelengths, the use of the compounds of general formula (I) according to the present invention as substrates for γ-GT leads to test systems which are much more sensitive than those previously used. The new substrates can be employed for the determination of the activity of γ-GT not only in biochemical but also in clinical-chemical fields.

Consequently, diagnostic agents which contain γ-glutamyl-4-azoanilides of general formula (I) display considerable advantages in comparison with the prior art. The greater sensitivity leads to a lowering of the limit of detection for γ-GT, to shorter reaction times and to smaller amounts of sample to be used and thus also to smaller disturbances by other components of the samples. Furthermore, more favourable measurement wavelengths also reduce the susceptibility of the method to disturbances by insoluble components, for example by turbidites.

Besides one or more of the substrates of general formula (I) according to the present invention, the diagnostic agents also contain an amino acid or a peptide as acceptor of the γ-glutamyl radical, an appropriate buffer system, as well as optionally further appropriate additives normally used for such diagnostic agents, for example wetting agents, stabilisers and the like. The diagnostic agent can be in the form of a solution, as a lyophilisate, as a powder mixture or as a reagent tablet or it can be applied to an absorbent carrier.

The diagnostic agent according to the present invention in the form of a solution preferably contains all the reagents needed for the test. As solvents, there can be used, for example, water or a mixture of water with a water-soluble organic solvent, for example methanol, ethanol, acetone or dimethylformamide. For reasons of storage stability, it can be advantageous to divide the reagents required for the test into two or more solutions which are first mixed at the time of making the actual investigation.

For the production of the diagnostic agent in the form of a lyophilisate with a total weight of from about 5 to 20 mg. and preferably of about 10 mg., a solution is dried which contains, in addition to all of the reagents required for the test, also conventional structure forms, for example polyvinylpyrrolidine, and possibly further filler materials, for example mannitol, sorbitol or xylitol.

A diagnostic agent in the form of a powder mixture or reagent tablet can be produced by mixing the components of the test with conventional galenical additives and then granulated. Additives of this kind include, for example, sugar alcohols, such as mannitol, sorbitol and xylitol, or other soluble, inert compounds, such as polyethylene glycols or polyvinylpyrrolidone. In general, the powder mixtures and reagent tablets have a final weight of about 30 to 200 mg. and preferably of from 50 to 80 mg.

For the production of the diagnostic agent in the form of a test strip, an absorbent carrier, preferably filter paper, cellulose or synthetic fibre fleece, is impregnated with solutions of the necessary reagents usually employed for the production of test strips in volatile solvents, for example water, methanol, ethanol or acetone. This can take place in one impregnation step. However, it is often desirable to carry out the impregnation in several steps, solutions thereby being used each of which contains a part of the components of the diagnostic agent. Thus, for example, in a first step, impregnation can be carried out with an aqueous solution which contains buffer and other water-soluble additives and then, in a second step, with a solution which contains the γ-GT substrate. The finished test paper can be used as such or can be stuck in known manner on to handles or preferably sealed between synthetic resins and fine meshes according to Federal Republic of Germany Patent Specification No. 21 18 455.

The following Examples describe some of the numerous process variants which can be used for the synthesis of the compounds according to the present invention, as well as, by way of example, the use of the new γ-glutamyl-4-azoanilides for the determination of activity of γ-glutamyl transferase.

EXAMPLE 1

2-Amino-5-[[4-(2-cyano-4-nitrophenyl)-azo-3-(2-carboxyethyl)-phenyl]-amino]-5-oxopentanoic acid diammonium salt (S1)

(a) 3-(3'-Aminophenyl)-propionic acid.

30 g. 3-Nitrobenzaldehyde and 30 g. malonic acid were heated in 60 ml. pyridine at a maximum temperature of 50° C. until a clear solution was obtained. Subsequently, 3 ml. piperidine were added thereto and the solution was heated for 1 hour at 80° C. Thereafter, it was heated under reflux for 3 hours. The solution was then poured into 400 ml. water which contained 50 ml. concentrated hydrochloric acid. The precipitated solid material was filtered off and washed with water. It was subsequently dissolved in 400 ml. water in which 8 g. sodium hydroxide had been dissolved. Insoluble materials were then filtered off and the 3-nitrocinnamic acid obtained was again precipitated out by acidification with hydrochloric acid. The compound was recrystallised from ethanol, the yield being 17 g.; m.p. 204° C.

15 g. 3-Nitrocinnamic acid were introduced into 100 ml. ethanol, together with 0.4 g. of a 5% palladium-on-charcoal catalyst. This suspension was reduced at atmospheric pressure and at ambient temperature with hydrogen and, after completion of the take up of hydrogen, a further 15 g. 3-nitrocinnamic acid were added thereto and the hydrogenation repeated. The catalyst was subsequently filtered off and the solution evaporated to dryness in a vacuum. Upon adding 50 ml. diethyl ether to the remaining viscous oil, a rapid crystallisation took place. There were obtained 20 g. 3-(3'- aminophenyl)-propionic acid in the form of a colourless solid; m.p. 73° C.

(b) Diazotisation of 2-cyano-4-nitroaniline.

A solution of nitrosylsulphuric acid was prepared by adding 1.4 g. sodium nitrite to 15 ml. 98% sulphuric acid, the temperature being maintained at less than 10° C. After completion of the addition of the sodium nitrite, the mixture was heated to 60° C. and stirred until a clear solution had formed. This solution was then cooled to below 20° C. and, while stirring vigorously, mixed with 0.02 mole of powdered 2-cyano-4-nitroaniline. The addition took place in such a manner that the temperature did not increase above 20° C. Subsequently, stirring was carried out for 45 minutes at 20° C. before the resulting solution of the diazonium salt was used for azo coupling with 3-(3'-aminophenyl)-propionic acid.

(c) Azo coupling of 2-cyano-4-nitrophenyldiazonium salt with 3-(3'-aminophenyl)-propionic acid.

0.02 mole 3-(3'-aminophenyl)-propionic acid was dissolved in 40 ml. 10% sulphuric acid. 50 g. ice were first added to this solution and then, while stirring and cooling to a temperature below 5° C., 0.02 mole of the diazonium salt solution produced in (b) above was slowly added thereto. After 2 hours, the reaction mixture was warmed to ambient temperature and stirred for a further 2 hours. 100 ml. Water and 50 g. ice were then added thereto and the precipitated azo coloured material was filtered off. The solid was washed neutral with water and then vigorously stirred in 125 ml. acetone. The coloured material was filtered off and dried at 50° C.; $\lambda_{max.} = 488$ nm; $\epsilon = 11.3$ cm$^2$ $\mu$mol$^{-1}$.

(d) N-Phthaloyl derivative of S1.

1 g. of the aminoazo derivative from (c) above and 1.5 g. N-phthaloylglutamic acid anhydride were dissolved in 30 ml. acetic acid. The solution was heated to 53° C. and stirred for 21 hours. The reaction mixture was then evaporated in a vacuum to a volume of 10 ml. The concentrated solution was poured into water and the precipitated product was filtered off.

(e) S1.

The N-phthaloyl-protected compound prepared in (d) above was mixed with 1 ml. hydrazine hydrate in 20 ml. methanol at 20° C. The mixture was stirred for 2 hours, then mixed with 50 ml. acetone and stirred for a further 2 hours. Subsequently, 1 ml. of a concentrated aqueous solution of ammonia was added thereto in order to precipitate out the N-glutamyl compound as the ammonium salt. The precipitated solid was filtered off and again dissolved in a minimum amount of distilled water. After again adding acetone, the product was again precipitated out, filtered off and dried. 0.92 g. S1 was obtained: $\lambda_{max.} = 394$ nm.

EXAMPLE 2

2-Amino-5-[[4-(2-cyano-4-nitrophenyl)-azo-3-(2-carboxyethoxy)-phenyl]-amino]-5-oxopentanoic acid diammonium salt (S2)

(a) 3-Aminophenoxyacetic acid.

45 g. 3-Acetylaminophenol, 28.5 g. chloroacetic acid and 24 g. sodium hydroxide were dissolved in 200 ml. water and heated under reflux for 30 minutes. Water was then distilled off until the first crystals began to separate out. At this stage, there was added thereto a solution of 14.3 g. chloroacetic acid in 100 ml. water. Subsequently thereto, a solution of 12 g. sodium hydroxide in 30 ml. water was added thereto. The reaction mixture was heated under reflux for 1 hour before acidifying the solution with about 25 ml. hydrochloric acid. After cooling the solution, the precipitated solid was filtered off, washed twice with 50 ml. amounts of water and dried.

The 3-acetylaminophenoxyacetic acid thus obtained was heated under reflux for 15 minutes in a mixture of 100 ml. water and concentrated hydrochloric acid. 300 ml. water were then added thereto and the solution adjusted to a pH value of 4 to 5 with ammonia solution. The precipitated solid was filtered off and washed with water which had been slightly acidified with acetic acid. There were thus obtained 36 g. 3-aminophenoxyacetic acid in the form of white crystals; m.p. 220° C.

(b) Azo coupling of 2-cyano-4-nitrophenyldiazonium salt with 3-aminophenoxyacetic acid.

The azo coupling took place in a manner analogous to that described in Example (1c) using 0.02 mole of each of the reaction components. The precipitated azo coloured material was filtered off, washed with acetone and dried at 50° C.; $\lambda_{max.} = 508$ nm; $\epsilon = 19.5$ cm$^2$ $\mu$mol$^{-1}$.

(c) N-Phthaloyl derivative of S2.

The acylation of the aminoazo derivative prepared in Example (2b) with N-phthaloylglutamic acid anhydride took place in a manner analogous to that described in Example (1d) using 1 g. of the coloured material. Instead of 1.5 g. N-phthaloylglutamic acid anhydride, there was used 1.3 g. of the acylation agent. The reaction time was 28 hours.

(d) S2.

The N-phthaloyl-protected compound prepared in Example (2c) was reacted in a manner analogous to that described in Example (1e). 0.14 g. S2 was thus obtained; $\lambda_{max.} = 414$ nm.

EXAMPLE 3

5-[(4-Amino-4-carboxyl-1-oxobutyl)-amino]-2-(4-nitrophenyl)-azobenzoic acid diammonium salt (S3)

(a) Nitrophenyldiazonium salt.

0.02 mole 4-nitroaniline was heated in a mixture of 10 ml. acetic acid and 10 ml. hydrochloric acid until a clear solution had formed. This solution was then poured, with vigorous stirring, on to a mixture of 40 g. ice and 10 ml. water. Immediately thereafter, there was added all at once a solution of 1.45 g. sodium nitrite in 10 ml. water which had been previously cooled to 0° C. The mixture was further stirred for 15 minutes and then excess nitrous acid was decomposed with some urea. The clear solution was, without further working up, used for the subsequent azo coupling.

(b) Azo coupling of 4-nitrophenyldiazonium salt with 3-aminobenzoic acid.

The N-methanesulphonate of 3-aminobenzoic acid was first prepared. For this purpose, 0.02 mole of the amine was dissolved in 4 ml. water which contained 0.8 g. sodium hydroxide. This solution was then added to a solution of 1.9 g. sodium bisulphite (Na$_2$S$_2$O$_5$) and 1.6 ml. of a 40% aqueous formaldehyde solution in 4 ml. water. The mixture was heated to 90° C. for 1 hour and then cooled to ambient temperature.

The solution of the N-methanesulphonate so prepared was diluted with 100 ml. ice water. 10 g. Sodium hydrogen carbonate were then added thereto. The diazonium salt solution prepared in Example (3a) was then slowly added thereto over a period of time of 30 minutes, care being taken that the temperature of the reaction mixture always remained below 10° C. Subsequently, stirring was carried out for 1 hour at ambient temperature.

The solution of the N-methanesulphonate of the aminoazo coloured material was then heated to 80° C. and mixed with a solution of 7 g. sodium hydroxide in 16 ml. water. A pH of 11–12 was thus achieved. The solution was kept at 80° C. for 15 minutes, then cooled to ambient temperature and acidified with concentrated hydrochloric acid to pH 3. The coloured material which thereupon precipitated out was filtered off, washed with water and dried; $\lambda_{max.}=404$ nm; $\epsilon=7.0$ cm$^2$ $\mu$mol$^{-1}$.

(c) N-Phthaloyl derivative of S3.

1 g. of the aminoazo coloured material and 1.8 g. N-phthaloylglutamic acid anhydride were stirred for 24 hours in 40 ml. boiling acetone. The reaction mixture was then evaporated to dryness in a vacuum. The residue was used for the removal of the protective group without further working up.

(d) S3.

The removal of the protective group in the case of the compound prepared in Example (3c) took place analogously to Examples (1e) and (2d). 0.18 g. of product was obtained; $\lambda_{max.}=314$ nm.

EXAMPLE 4

2-Amino-5-[[4-(2,5-dichloro-4-nitrophenyl)-azo-3-(carboxymethoxy)-phenyl]-amino]-5-oxopentanoic acid diammonium salt (S4)

(a) 2,5-Dichloro-4-nitrophenyldiazonium salt.

This was prepared by diazotising 2,5-dichloro-4-nitroaniline analogously to Example (3a).

(b) Azo coupling of 2,5-dichloro-4-nitrophenyldiazonium salt with 3-aminophenoxyacetic acid.

The azo coupling of the diazonium salt prepared in (a) with 3-aminophenoxyacetic acid was carried out analogously to the methods described in Examples (1c) and (2b) using 0.02 mole of each of the reaction components. The azo coloured material obtained was filtered off, washed with acetone and dried at 50° C.; $\lambda_{max.}=460$ nm; $\epsilon=13.4$ cm$^2$ $\mu$mol$^{-1}$.

(c) N-Phthaloyl derivatives of S4.

The acylation of the aminoazo coloured material from (b) took place analogously to Example (1d) with 1 g. of coloured material. Instead of 1.5 g. N-phthaloylglutamic acid anhydride, there was used 1.2 g. thereof. The reaction mixture was heated under reflux for 5 minutes.

(d) S4.

The compound prepared in (c) was reacted analogously to Examples (1e), (2d) or (3d). 0.26 g. of S4 was obtained; $\lambda_{max.}=402$ nm.

EXAMPLE 5

2-Amino-5-[[3-(2-carboxyethyl)-4-(2,4-dicyano-3-methyl-5-thienyl)-azophenyl]-amino]-5-oxopentanoic acid diammonium salt (S5)

(a) Diazotisation of 2-amino-3,5-dicyano-4-methylthiophene.

2-Amino-3,5-dicyano-4-methylthiophene was diazotised analogously to Example (1b).

(b) Azo coupling of the diazonium salt of 2-amino-3,5-dicyano-4-methylthiophene with 3-(3'-aminophenyl)propionic acid.

The azo coupling took place analogously to Example (1c) with 0.02 mole of each of the reaction components. The azo dyestuff obtained was filtered off, washed with acetone and dried at 50° C.; $\lambda_{max.}=530$ nm; $\epsilon=14.3$ cm$^2$ $\mu$mol$^{-1}$.

(c) N-Phthaloyl derivative of S5.

The acylation of the azo dyestuff from (b) took place analogously to Example (1d) with 1 g. of coloured material. However, instead of 1.5 g. N-phthaloylglutamic acid anhydride, there was only used 1 g. thereof. The reaction mixture was heated under reflux for 2 minutes.

(d) S5.

The removal of the protective group from the compound prepared in (c) took place analogously to Examples (1e) and (2d). There was obtained 0.14 g. of S5; $\lambda_{max.}=434$ nm.

EXAMPLE 6

2-Amino-5-[[3-carboxymethoxy-4-(2,4-dicyano-3-methyl-5-thienyl)-azophenyl]-amino]-5-oxopentanoic acid diammonium salt (S6).

(a) Azo coupling of the diazonium salt of 2-amino-3,5-dicyano-4-methylthiophene with 3-aminophenoxyacetic acid.

The azo coupling of the diazonium salt of 2-amino-3,5-dicyano-4-methylthiophene from Example (5a) with 3-aminophenoxyacetic acid from Example (2a) took place analogously to Example (5b) with 0.02 mole of each of the reaction components. The aminoazo coloured material obtained was filtered off, washed with acetone and dried at 50° C.; $\lambda_{max.}=538$ nm; $\epsilon=26.8$ cm$^2$ $\mu$mol$^{-1}$.

(b) N-Phthaloyl derivative of S6.

The acylation of the aminoazo coloured material from (a) with N-phthaloylglutamic acid anhydride took place analogously to Example (5c) with 1 g. of coloured material. Instead of 1 g. N-phthaloylglutamic acid anhydride, there was used 1.2 g. thereof.

(c) S6.

The N-phthaloyl protective group in the compound prepared in (b) was removed analogously to Examples 1 to 5. There was obtained 0.84 g. of S6; $\lambda_{max.}=448$ nm.

EXAMPLE 7

2-Amino-5-[[4-(5-carboxy-4-methyl-2-thiazolyl)-3-methylazophenyl]-amino]-5-oxopentanoic acid diammonium salt (S7)

(a) Diazotisation of 2-amino-5-carboxy-4-methylthiazole.

A solution of nitrosylsulphuric acid was prepared by adding 1.4 g. sodium nitrite to 6 ml. 98% sulphuric acid. When adding the sodium nitrite, care was taken that the temperature in the solution always remained below 10° C. The mixture was subsequently heated to 60° C. and stirred until the solution was clear. The solution was then kept at about 30° C. in order to prevent crystallisation.

A solution of 0.02 mole 2-amino-5-carboxy-4-methylthiazole in a mixture of 2 ml. 77% sulphuric acid and 6 ml. water was added to a mixture of 21 ml. 77% sulphuric acid and 12 ml. water. The resultant solution was cooled to −10° C. The nitrosylsulphuric acid was slowly added thereto, taking care that the temperature in the solution always remained below −10° C. Subsequently, the reaction mixture was stirred at this temperature for 30 minutes and then at −5° C. for a further 30 minutes. The solution was thereafter diluted with a mixture of 100 g. ice and 100 ml. water. Excess nitrous acid was decomposed by the addition of urea. The diazonium salt solution thus obtained was used directly for the azo coupling.

(b) Azo coupling of the diazonium salt of 2-amino-5-carboxy-4-methylthiazole with 3-methylaniline.

The azo coupling of the diazonium salt of 2-amino-5-carboxy-4-methylthiazole with 3-methylaniline was carried out analogously to the method described in Examples 1, 2, 4, 5, and 6, 0.02 moles of each reaction component being used. The precipitated azo coloured material was filtered off, washed with acetone and dried at 50° C.; $\lambda_{max.}=495$ nm; $\epsilon-19.7$ cm$^2$ $\mu$mol$^{-1}$.

(c) N-Phthaloyl derivative of S7.

The acylation of the aminoazo coloured material obtained in (b) with N-phthaloylglutamic acid anhydride took place analogously to the method described in Example (1d). In this case, 1 g. of the coloured material was stirred for 48 hours at ambient temperature with 1.2 g. N-phthaloylglutamic acid anhydride.

(d) S7.

The removal of the N-phthaloyl protective group from the compound prepared in (c) took place analogously to the method described in Examples 1 to 6. 0.21 g. of product was obtained; $\lambda_{max.}=412$ nm.

EXAMPLE 8

2-Amino-5-[[3-(2-carboxyethyl)-4-(5-cyano-4-methyl-2-thiazolyl)-azophenyl]-amino]-5-oxopentanoic acid diammonium salt (S8)

(a) Azo coupling of the diazonium salt of 2-amino-5-cyano-4-methylthiazole with 3-(3'-aminophenyl)propionic acid.

The diazonium salt of 2-amino-5-cyano-4-methylthiazole, prepared analogously to Example (7a), was coupled with 3-(3'-aminophenyl)-propionic acid analogously to the method described in Example (7b). In this case, 0.02 mole of each of the reaction components was used. The aminoazo coloured material obtained was filtered off, washed with acetone and dried at 50° C.; $\lambda_{max}=520$ nm; $\epsilon=29.7$ cm$^2$ $\mu$mol$^{-1}$.

(b) N-Phthaloyl derivative of S8.

1 g. of the coloured material obtained in (a) was heated under reflux for 18 hours with 1 g. N-phthaloylglutamic acid anhydride in a mixture of 40 ml. acetone and 10 ml. acetic acid. Subsequently, the solvent was removed in a vacuum. The residue was subjected directly to the removal of the protective group without further purification.

(c) S8.

The N-phthaloyl protective group in the compound prepared in (b) was removed according to the method described in Examples 1 to 7. 0.84 g. of S8 was obtained; $\lambda_{max.}=420$ nm.

EXAMPLE 9

2-Amino-5-[[3-(2-carboxyethyl)-4-(2-thiazolyl)-azophenyl]-amino]-5-oxopentanoic acid diammonium salt (S9)

(a) Azo coupling of the diazonium salt of 2-aminothiazole with 3-(3'-aminophenyl)-propionic acid.

The azo coupling of the diazonium salt of 2-aminothiazole, prepared analogously to Example (7a), with 3-(3'-aminophenyl)-propionic acid took place analogously to the method described in Examples 1, 2, 5, 6, 7 and 8. In this case, 0.02 mole of each of the reaction components was used. The aminoazo coloured material obtained was filtered off, washed with acetone and dried at 50° C.; $\lambda_{max.}=470$ nm; $\epsilon=17.0$ cm$^2$ $\mu$mol$^{-1}$.

(b) N-Phthaloyl derivative of S9.

The acylation of the aminoazo coloured material obtained in (a) with N-phthaloylglutamic acid anhydride took place analogously to the process described in Example (7c) using 1 g. of coloured material. Instead of 1.2 g. of the acylation agent, the coloured material was stirred for 24 hours at ambient temperature with 1.1 g. N-phthaloylglutamic acid anhydride.

(c) S9.

The removal of the N-phthaloyl protective group from the compound prepared in (b) took place analogously to the method described in Examples 1 to 8. 0.25 g. of S9 was thus obtained; $\lambda_{max.}=394$ nm.

EXAMPLE 10

2-Amino-5-[[3-(2-carboxylatoethyl)-4-(3-methyl-thiazolium-2-yl)-azophenyl]-amino]-5-oxopentanoic acid ammonium salt (S10)

1 g. of the compound obtained in Example (9c) was dissolved in a mixture of 20 ml. chlorobenzene and 20 ml. dichloromethane. 2 ml. acid-free dimethyl sulphate were added to this solution. In order to ensure that the dimethyl sulphate used was free from traces of acid, the dimethyl sulphate used was one which had immediately previously been washed with water and subsequently dried with anhydrous sodium sulphate. The reaction mixture was stirred for 24 hours at ambient temperature. Precipitated solid material was then filtered off and the solid material washed first with a little dichloromethane and then with a little acetone. Subsequently, the solid material was mixed with a small amount of methanol which contained two drops of acetic acid and stirred for 2 hours. The solid material was then filtered off, washed with a small amount of methanol and subsequently dried. 0.23 g. of S10 was thus obtained; $\lambda_{max.}$ (substrate)$=402$ nm; $\lambda_{max.}$ (coloured material)$=486$ nm; $\epsilon=15.5$ cm$^2$ $\mu$mol$^{-1}$.

EXAMPLE 11

2-Amino-5-[[3-carboxymethoxy-4-(6-nitro-2,1-benzisothiazol-3-yl)-azophenyl]-amino]-5-oxopentanoic acid diammonium salt (S11)

(a) Diazotisation of 3-amino-5-nitrobenzisothiazole.

A solution of nitrosylsulphuric acid was prepared by adding 0.75 g. sodium nitrite to 10 ml. 98% sulphuric acid at a temperature below 10° C. The mixture was heated to 60° C. and stirred until a clear solution was obtained.

0.01 mole 3-amino-5-nitrobenzisothiazole was dissolved in 10 ml. 85% sulphuric acid and the solution cooled to below 10° C. The cooled nitrosylsulphuric acid solution was added to this amine solution with vigorous stirring while maintaining the temperature below 10° C. After 2.5 hours, excess nitrous acid was decomposed by the addition of urea. The diazonium salt solution thus obtained was used for the azo coupling without further working up.

(b) Azo coupling of the diazonium salt of 3-amino-5-nitrobenzisothiazole with 3-aminophenoxyacetic acid.

0.01 mole 3-aminophenoxyacetic acid was dissolved in 10 ml. of a mixture of 1 part by volume of propionic acid and 5 parts by volume of acetic acid. 20 g. of ice and 80 ml. water were added to this solution. Subsequently, 20 g. sodium acetate trihydrate were added thereto. The diazonium salt solution prepared in (a) was slowly added to this mixture with cooling, taking care that the temperature always remained below 10° C. In order to maintain a pH value greater than 4, if necessary further sodium acetate was added thereto. After stirring for 12 hours at ambient temperature, the mixture was diluted with 500 ml. hot water and the azo coloured material which thereupon precipitated out was filtered off, washed with water and dried. Purification took place by thoroughly triturating with a small amount of acetone and subsequent filtration and drying of the coloured material thus obtained; $\lambda_{max.} = 560$ nm; $\epsilon = 2.2$ cm² µmol⁻¹.

(c) N-Phthaloyl derivative of S11.

1 g. of the azo coloured material prepared in (b) was acylated with N-phthaloylglutamic acid anhydride analogously to Example (8b). In this case, instead of 18 hours, the reaction mixture was only heated under reflux for 7 hours.

(d) S11.

The N-phthaloyl-protected compound prepared in (c) was reacted with hydrazine analogously to the method described in the preceding Examples in order to remove the N-phthaloyl protective group. 0.70 g. of product was obtained; $\lambda_{max.} = 453$ nm.

EXAMPLE 12

2-Amino-5-[[4-(2-butylthio-1,3,4-thiadiazol-5-yl)-3-carboxymethoxyazophenyl]-amino]-5-oxopentanoic acid diammonium salt (S12)

(a) Azo coupling of the diazonium salt of 2-amino-5-(n-butylthio)-1,3,4-thiadiazole with 3-aminophenoxyacetic acid.

The diazonium salt of 2-amino-5-(n-butylthio)-1,3,4-thiadiazole, prepared analogously to Example (11a), was coupled with 3-aminophenoxyacetic acid analogously to Example (1c) or (2b). There were used 0.02 mole of each of the reaction components. The precipitated coloured material was filtered off, washed with acetone and dried at 50° C.; $\lambda_{max.} = 490$ nm; $\epsilon = 15.2$ cm² µmol⁻¹.

(b) N-Phthaloyl derivative of S12.

The acylation of 1 g. of the aminoazo coloured material obtained in (a) with 1.2 g. N-phthaloylglutamic acid anhydride took place analogously to Example (7c) or (9b). The reaction mixture was heated under reflux for 1 minute.

(c) S12.

The removal of the protective group from the compound obtained in (b) was carried out analogously to the method described in the preceding Examples. 0.32 g. of product was thus obtained; $\lambda_{max.} = 424$ nm.

EXAMPLE 13

2-Amino-5-[[3-carboxymethoxy-4-(6-ethoxy-2-benzothiazolyl)-azophenyl]-amino]-5-oxopentanoic acid diammonium salt (S13).

(a) Azo coupling of the diazonium salt of 2-amino-6-ethoxybenzthiazole with 3-aminophenoxyacetic acid.

The diazonium salt of 2-amino-6-ethoxybenzthiazole, prepared analogously to Example (7a), was coupled with 3-aminophenoxyacetic acid analogously to the method described in Example (7b). For this purpose, there was used 0.02 mole of each of the reaction components. The precipitated coloured material was filtered off, washed with acetone and dried at 50° C.; $\lambda_{max.} = 494$ nm; $\epsilon = 24.0$ cm² µmol⁻¹.

(b) N-Phthaloyl derivative of S13.

The acylation of 1 g. of the aminoazo coloured material prepared in (a) took place with 0.8 g. N-phthaloylglutamic acid anhydride analogously to the method described in Example (9b). The reaction mixture was heated under reflux for 2 minutes and subsequently evaporated to dryness in a vacuum. The residue was used for the removal of the protective group without further working up.

(c) S13.

The removal of the N-phthaloyl protective group from the compound prepared in (b) took place in a manner analogous to that described in Example (1e). 0.9 g. of S13 was thus obtained; $\lambda_{max.} = 449$ nm.

EXAMPLE 14

Determination of the activity of γ-glutamyl transferase (a) Reagent.

21.78 g. Glycylglycine were dissolved in about 900 ml. distilled water, the pH was adjusted to 7.9 with 2N aqueous sodium hydroxide solution, the amount of substrate calculated for a concentration of 1 mmole/liter was dissolved therein and the solution made up to 1000 ml. with distilled water. End concentration in the test: glycylglycine 150 mmole/liter, pH 7.9 substrate 1 mmole/liter.

(b) Carrying out of the measurement.

2.0 ml. of the reagent described in (a) was pipetted into a cuvette, tempered to 25° C. and mixed with 0.2 ml. of sample. The extinction increase per minute was measured at an appropriate wavelength.

(c) Calculation of the activity.

One international unit (U) is the enzyme activity which converts 1 µmole of substrate per minute at 25° C. The activity of the γ-glutamyl transferase in U/liter in the sample is calculated according to the following equation:

$$U/l. = \frac{\Delta E/\text{min.} \times V \times 1000}{\epsilon \times v \times d}$$

wherein ΔE/min is the extinction increase at an appropriate wavelength per minute, V is the batch volume in ml., v is the sample volume in ml., ε is the extinction coefficient in cm² µmol⁻¹ and d is the layer thickness of the cuvette in cm.

(d) Results.

In the case of the investigation of the same control serum with different substrates, there were determined the activities for γ-GT set out in the following Table:

| substance | measurement wavelength (nm) | extinction coefficient (cm² µmol⁻¹) | U/liter at 25° C. |
|---|---|---|---|
| S1 | 546 | 7.8 | 144 |
| S5 | 578 | 8.9 | 77 |
| S8 | 546 | 25.2 | 101 |
| S9 | 546 | 2.8 | 160 |

(e) Comparison

For the comparison with the values found under (d), the same control serum was investigated with the previously usual substrate L-γ-glutamyl-3-carboxy-4-nitroanilide (L-Glupa C):

| substance | measurement wavelength (nm) | extinction coefficient (cm² μmol⁻¹) | U/liter at 25° C. |
|---|---|---|---|
| L-Glupa C | 405 | 9.5 | 128 |

EXAMPLE 15

Determination of the activity of γ-GT at 25° and 37° C. with S1 and L-Glupa C

Analogously to Example 14, the activities of γ-GT were determined at 25° and 37° C. in three mixtures of human sera in three different activity ranges, as well as in a control serum. The substrates used were L-Glupa C and S1. The following values were found:

| sample | with L-Glupa C 25° C. U/l. | with L-Glupa C 37° C. U/l. | with S1 25° C. U/l. | with S1 37° C. U/l. |
|---|---|---|---|---|
| human serum pool 1 | 35 | 57 | 42 | 96 |
| human serum pool 2 | 63 | 106 | 76 | 176 |
| human serum pool 3 | 190 | 323 | 220 | 490 |
| control serum PPU 516 | 139 | 211 | 134 | 268 |

It will be understood that the specification and examples are illustrative but not limitative of the present invention and that other embodiments within the spirit and scope of the invention will suggest themselves to those skilled in the art.

What is claimed is:

1. In a method for the determination of gamma-glutamyl transferase wherein the transferase liberates a colored product from a substrate in the presence of an amino acid or peptide acceptor, and the rate of release of the colored product is measured optically as a measure of the transferase activity, the improvement comprising using, as the substrate, the compound of the formula

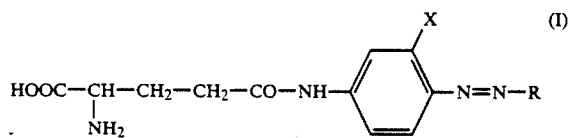

wherein

X is $C_1-C_7$ alkyl, $-(CH_2)_m-COOH$ or $-O-(CH_2)_n-COOH$ wherein m is 0, 1, 2, 3 or 4 and n is 1, 2, 3 or 4;

R is p-nitrophenyl; p-nitrophenyl substituted one or more times by halogen, cyano, $C_1-C_7$ alkoxy, hydroxyl, $C_1-C_7$ alkyl, carboxy-$C_1-C_7$-alkyl, amino, $C_1-C_7$-alkyl-amino or di-$C_1-C_7$-alkyl-amino, the substituents being the same or different; or R is a thiophene, a thiophene substituted one or more times by cyano, nitro, $C_1-C_7$ alkyl or carboxy-$C_1-C_7$-alkyl, the substituents being the same or different; or R is a thiazole; a thiazole substituted one or more times by cyano, carboxyl or $C_1-C_7$ alkyl, the substituents being the same or different; or R is a benzothiazole, a benzothiazole substituted one or more times by $C_1-C_7$-alkoxy; or R is a benzoisothiazole; a benzoisothiazole which is substituted one or more times by nitro; or R is an N-$C_1-C_7$ alkyl-thiazole; a 1,3,5-thiodiazole or a 1,3,5-thiodazole which is substituted one or more times by $C_1-C_7$alkylthio; or an alkali metal, alkaline earth metal or ammonium salt thereof.

2. The method of claim 1 wherein each alkyl or alkoxy is selected from the group consisting of methyl, ethyl, methoxy and ethoxy.

3. The method of claim 1 wherein the alkali metal salts are lithium, sodium, potassium, rubidium or caesium salts and the alkaline earth metal salts are magnesium, calcium, strontium or barium salts and the ammonium salts contain ammonium ions which are unsubstituted or are substituted 1 to 4 times by $C_1-C_7$ alkyl or $C_6-C_{10}$-ara-$C_1-C_7$ alkyl.

4. The method of claim 1 wherein the salts are lithium, sodium, potassium, magnesium, calcium, unsubstituted ammonium or ammonium ions substituted with $C_1-C_7$ alkyl or benzyl.

5. In a diagnostic agent for the determination of the activity of the enzyme gamma-glutamyl transferase containing at least one chromogenic substrate, an amino acid or a peptide acceptor and a buffer system, as well as an adjuvant, the improvement comprising using as said chromogenic substrate the compound of claim 1.

6. In a method for the determination of gamma-glutamyl transferase wherein the transferase liberates a colored product from a substrate in the present of an amino acid or peptide acceptor, and the rate of release of the colored product is measured optically as a measure of the transferase activity, the improvement comprising using, as the substrate at least one of the compounds selected from the group consisting of 2-amino-5-[[4-(2-cyano-4-nitrophenyl)-azo-3-(2-carboxyethyl)phenyl]-amino]-5-oxopentanoic acid, 2-amino-5-[[4-(2-cyano-4-nitrophenyl)-azo-3-(2-carboxyethoxy)phenyl]-amino]-5-oxopentanoic acid, 2-amino-5-[[3-(carboxy-4-(4-nitrophenyl)-azophenyl]-amino]-5-oxopentanoic acid, 2-amino-5[[4-(2,5-dichloro-4-nitrophenyl)-azo-3-(carboxymethoxy)-phenyl]-amino]-5-oxopentanoic acid, 2-amino-5-[[3-(2-carboxyethyl)-4-(2,4-dicyano-3-methyl-5-thienyl)-azophenyl]-amino]-5-oxopentanoic acid, 2-amino-5-[[3-carboxymethoxy-4-(2,4-dicyano-3-methyl-5-thienyl-azophenyl]-amino]-5-oxopentanoic acid, 2-amino-5-[[4-(5-carboxy-4-methyl-2-thiazolyl-3-methylazophenyl]-amino]-5-oxopentanoic acid, 2-amino-5-[[3-(2-carboxyethyl)-4-(5-cyano-4-methyl-2-thiazolyl)-azophenyl]amino]-5-oxopentanoic acid, 2-amino-5-[[3-(2-carboxyethyl)-4-(2-thiazolyl)azophenyl]-amino]-5-oxopentanoic acid, 2-amino-5-[[3-(2-carboxylatoethyl)-4-(3-methyl-thiazolium-2-yl)-azophenyl]-amino]-5-oxopentanoic acid, 2-amino-5-[[3-carboxymethoxy-4-(6-nitro-2,1-benzisothiazol-3-yl)-azophenyl]-amino]-5-oxopentanoic acid, 2-amino-5-[[4-(2-butylthio-1,3,4-thiadiazol-5-yl)-3-carboxymethoxyazophenyl]-amino]-5-oxopentanoic acid, 2-amino-5-[[3-carboxymethoxy-4-(6-ethoxy-2-benzothiazolyl)azophenyl]-amino]-5-oxopentanoic acid and the alkali metal, alkaline earth metal or ammonium salts thereof.

7. In a diagnostic agent for the determination of the activity of the enzyme gamma-glutamyl transferase containing at least one chromogenic substrate, an amino acid or a peptide acceptor and a buffer system, as well as, an adjuvant the improvement comprising using as said chromogenic substrate at least one of the compound of claim 6.

* * * * *

UNITED STATES PATENT AND TRADEMARK OFFICE
CERTIFICATE OF CORRECTION

PATENT NO. : 4,943,526

DATED : July 24, 1990

INVENTOR(S) : Elli Rauscher et al.

It is certified that error appears in the above-identified patent and that said Letters Patent is hereby corrected as shown below:

Col. 4, line 29: change "chromatography" to -- chromatographically --.

Col. 11, line 11: change "$\epsilon$ -19.7" to -- $\epsilon = 19.7$ --.

Signed and Sealed this

Twenty-third Day of June, 1992

Attest:

DOUGLAS B. COMER

Attesting Officer

Acting Commissioner of Patents and Trademarks